US00PP30011P3

(12) United States Plant Patent
Cain

(10) Patent No.: US PP30,011 P3
(45) Date of Patent: Dec. 25, 2018

(54) SWEET CHERRY TREE NAMED 'IFG CHER-THREE'

(50) Latin Name: *Prunus avium*
Varietal Denomination: IFG Cher-three

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 7 days.

(21) Appl. No.: 15/530,634

(22) Filed: Feb. 13, 2017

(65) Prior Publication Data

US 2018/0235122 P1 Aug. 16, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
See application file for complete search history.

*Primary Examiner* — Keith O. Robinson

(57) ABSTRACT

This invention is a new and distinct sweet cherry tree denominated 'IFG Cher-three'. The new sweet cherry tree is characterized by producing medium sized dark red fruits having reniform shape. Fruits ripen early about Apr. 23, 2014 in Delano Calif. The 'IFG Cher-three' has very firm, medium acid fruit with a good cherry flavor. Fruits are tolerant of rain induced cracking and high temperature induced double fruit. The tree has a medium low chilling requirement of approximately 300 to 400 hours.

1 Drawing Sheet

Latin name of the genus and species claimed: *Prunus avium.*

Variety denomination: 'IFG Cher-three'.

BACKGROUND OF THE INVENTION

The new and distinct sweet cherry tree described and claimed herein originated from open pollinated seeds of fruits of an early ripening unidentified female parent located in Bakersfield, Kern County, Calif. collected in May 2001. The male parent is unknown. The seeds were stratified, germinated and the resulting 285 seedlings were planted in the field near Delano, Kern County, Calif. in April 2002. The present variety of sweet cherry tree was selected as a single plant in May 2005 and was first asexually propagated in January 2006 by grafting onto *Prunus mahalab* rootstock. This propagule was found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-three' is characterized by producing medium size dark red fruits having reniform shape. Fruits ripen early about three to five days ahead of the 'Brooks' variety (U.S. Plant Pat. No. 6,676). The 'IFG Cher-three' has very firm, medium acid fruit with a good cherry flavor. Fruits are tolerant of rain induced cracking. The tree has a medium low chilling requirement of about 300 to 400 hours, slightly lower than the 'Brooks' variety of about 500 hours. It produces fewer doubled and spurred fruits as compared to the 'Brooks' variety in high summer temperature regions such as the Southern San Joaquin Valley of Calif. Fruits of 'IFG Cher-three' have medium long, thick stems that remain attached and stay green during storage and shipping.

In comparison to the 'Brooks' variety, which is a major variety grown in warm regions, the present variety ripens about three to five days earlier, and has more desirable darker red skin and flesh. It also has fewer undesirable doubled and spurred fruits as compared to 'Brooks' and has superior storage characteristics. In comparison to its female parent, the present variety has larger, firmer fruits. In comparison to the Tulare (U.S. Plant Pat. No. 6,407), the 'IFG Cher-three' produces fruit that ripen approximately six to eight days earlier.

BRIEF DESCRIPTION OF THE DRAWING

The accompanying photographic drawing in FIG. 1 illustrates in full color 'IFG Cher-three', taken from an 8-year old tree. The photograph was taken outdoors with indirect lighting. The colors are as nearly true as is reasonably possible in a color representation of this type.

An actively growing shoot tip collected at harvest can be seen in the upper portion of the drawing.

Typical mature fruit and fruit in cross-section are displayed on the lower half of the drawing. Typical cleaned and dried fruit pits are displayed on the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-three' plants grown in the vicinity of Delano, Kern County, Calif. during 2013 to 2014, and is believed to apply to plants of the variety grown under similar conditions of soil and climate elsewhere:

Tree:

General:

*Age*.—8 yrs. old.
*Height*.—About 2.4 M when pruned.
*Width*.—About 3.2 M when pruned.
*Vigor*.—Medium.
*Density of foliage*.—Medium.
*Form*.—Spreading.
*Branching*.—Strong.
*Resistance to*.—Insects: Average typical of *Prunus avium* species. Diseases: Average typical of *Prunus avium* species.
*Chilling requirements*.—Low.
*Graft compatibility*.—Good; produces compatible graft unions with *Prunus avium*, 'Mazzard' seedling (non-patented) and *Prunus mahaleb* seedlings (non-patented).

Trunk:

*Trunk diameter of* 8 *year old trees,* 30 *cm above the soil line*.—About 17.7 cm.
*Lenticel size*.—Medium.
*Lenticels dimensions*.—Length. About 6 mm. Width: About 2 mm.
*Lenticel shape*.—Elliptical shape oriented horizontally.
*Lenticel color*.—Greyed-orange: 196B.
*Trunk surface texture*.—Medium.
*Bark color*.—Brown: N200C.

Branches:

1-year old wood:

*Vertical top growth length*.—Medium: About 58.8 cm.
*Horizontal growth length*.—Medium: About 46.5 cm.
*Diameter*.—Vertical growth: About 0.9 cm. Horizontal growth: About 0.8 cm.
*Internode length*.—Short: About 2.8 cm.
*Number of lenticels*.—Few: approximately 5 lenticels per linear cm.
*Lenticel size*.—Small.
*Lenticel dimensions*.—Length: About 0.1 cm. Width: About 0.1 cm.
*Lenticel shape*.—Round.
*Bark color*.—The following colors were observed: Greyed-red: 178A and Greyed-orange: 177B.

2-year old wood:

*Length*.—Short: About 31.4 cm.
*Diameter*.—About 1.1 cm.
*Internode length*.—Short: About 2.5 cm.
*Number of lenticels*.—Few: Approximately 4 lenticels per linear cm.
*Lenticel size*.—Small.
*Lenticel dimensions*.—Length: About 0.3 cm. Width: About 0.1 cm.
*Lenticel shape*.—Elliptical shape oriented horizontally.
*Bark color*.—The following colors were observed: Greyed-orange: 177B and 177C.

Buds:

Vegetative buds:

*Shape*.—Elongated.
*Vegetative bud dimensions*.—Length: About 0.7 cm. Width: About 0.3 cm.
*Vegetative bud burst*.—Feb. 8, 2014.

Flower buds:

*Flower bud dimensions*.—Length: About 1.0 cm. Width: About 0.4 cm.
*Shape*.—Oval.
*Placement*.—At bud positions 1 to 8 on 1-year wood.
*Average number of flower buds on first year wood*.—About 7.
*Number of flower buds per spur on second year wood*.—2 to 4. Average: About 3.
*Color*.—The following colors were observed: Greyed-orange: 166A and 177A.
*Flower bud burst*.—Feb. 11, 2014.

Leaves:

Mature leaves:

*Leaf size*.—Small.
*Leaf dimensions*.—Length: About 14.6 cm. Width: About 6.1 cm.
*Leaf shape*.—Elongated ovate: Symmetric on both sides of central axis.
*Shape of tip*.—Acute: broadly.
*Shape of base*.—Oblique.
*Margin*.—Serrated: regular: pointed.
*Leaf profile*.—Involute.

Upper surface:

*Upper surface pubescence*.—None.
*Upper leaf surface color*.—Green: 137A.
*Surface texture*.—Smooth.

Lower surface:

*Lower surface pubescence*.—Medium to slightly dense.
*Lower leaf surface color*.—Yellow-green: 146A.

Petiole:

*Petiole dimensions*.—Length: About 2.9 cm. Width: About 0.2 cm.
*Upper surface of petiole color*.—Greyed-orange: 166A.
*Lower surface of petiole color*.—Yellow-green: 146D.
*Petiole groove*.—Narrow: Approximately 0.5 mm.
*Petiole pubescence*.—Very sparse.
*Venation*.—Arcuate.
*Vein color*.—Yellow-green: 144D.

Glands:

*Number of glands*.—2 to 4.
*Gland dimensions*.—Length: About 2.0 mm. Width: About 1.6 mm.
*Gland shape*.—Globose.
*Gland location*.—On petiole.

*Gland color*.—The following colors were observed: Greyed-red: 179A and 181C.
*Leaf stipule*.—Not present.

Flowers:
*Blooming period*.—Early.
*Blooming dates*.—First Bloom: Feb. 15, 2014. Full Bloom: Mar. 6, 2014.
*Number of flowers per cluster*.—2 to 4. Average: About 3.
*Corolla*.—Composed of unfused petals, somewhat overlapping.
*Corolla diameter*.—About 3.7 cm.
*Petal number*.—5.
*Petal length*.—About 1.5 cm.
*Petal width*.—About 1.4 cm.
*Margin waviness*.—Medium.
*Division of upper margin*.—Notched.
*Color of petal upper surface*.—White: 155C.
*Color of petal lower surface*.—White: 155C.
*Peduncle*.—Length: About 2.1 cm. Width: About 1.4 mm.
*Peduncle color*.—Yellow-green: 144A.
*Number of sepals*.—5.
*Sepal length*.—About 0.6 cm.
*Sepal width*.—About 0.5 cm.
*Sepal shape*.—Triangular.
*Sepal color*.—Upper surface: Yellow-green: 144A. Lower surface: Yellow-green: 144A.
*Filament*.—Length: About 0.4 to 1.7 cm. Width: About 0.4 mm.
*Filament color*.—White: N155A.
*Anther color*.—Greyed-yellow: 162A.
*Pollen color*.—Greyed-orange: 163A.
*Pollen production*.—High.
*Self-compatibility of flowers*.—Self-incompatible.
*Pollen compatibility group*.—S3S6.

Fruit:
General:
*Ripening period*.—Early: Approximately: Apr. 23, 2014.
*Use*.—Fresh market.
*Keeping quality*.—Average: similar to 'Brooks' variety.
*% Titratable acidity*.—About 0.99%.
*Refractometer test*.—Soluble solids; Brix — About 20.4.
*Firmtech II* ($g/mm^2$).—About 261.
*Juice color*.—Greyed-purple: 187C.
*Juice amount*.—Intermediate.
*Eating quality*.—Excellent good sugar/acid balance and firm texture.

Stem:
*Stem*.—Length: About 3.9 cm. Width: About 0.2 cm.
*Stem color*.—Yellow-green: 144A.
*Stem cavity*.—Medium deep.
*Stem retention during storage*.—Very good.
*Stem storage quality*.—Moderate to good.

Berry:
*Uniformity of size*.—Uniform.
*Shape*.—Reniform.
*Fruit weight*.—About 6.9 gm.
*Apical diameter*.—About 2.2 cm.
*Diameter transversely across suture*.—About 2.4 cm.
*Diameter at right angle to suture plane*.—About 2.0 cm.
*Suture*.—None.
*Percent of excessively deep or split sutures*.—About 0%.
*Doubles*.—0%.

Skin:
*Texture*.—Somewhat rough.
*Skin color*.—The following colors were observed: Greyed-purple: 187A and B.
*Tendency to tip crack*.—Not susceptible.
*Tendency to stem cavity crack*.—Not susceptible.

Flesh:
*Texture*.—Very firm.
*Color*.—The following colors were observed: Greyed-purple: 187B and 187C.

Stone:
*Shape*.—Oblong.
*Stone dimensions*.—Length: About 1.1 cm. Width: About 0.7 cm.
*Type*.—Freestone.
*Surface texture*.—Smooth.
*Stone color when dry*.—Orange-white: 159A.
*Tendency to split*.—None.
*Base*.—Rounded.
*Apex*.—Rounded.
*Ventral edge*.—Narrow suture protruding somewhat beyond the horizontal plane of the base of the stone, subtended by 2 prominent ridges converging at the base and the apex of the stone.
*Dorsal edge*.—Small, narrow ridge extending from the base to the apex of the stone.

What is claimed:

1. A new and distinct variety of sweet cherry tree as herein illustrated and described.

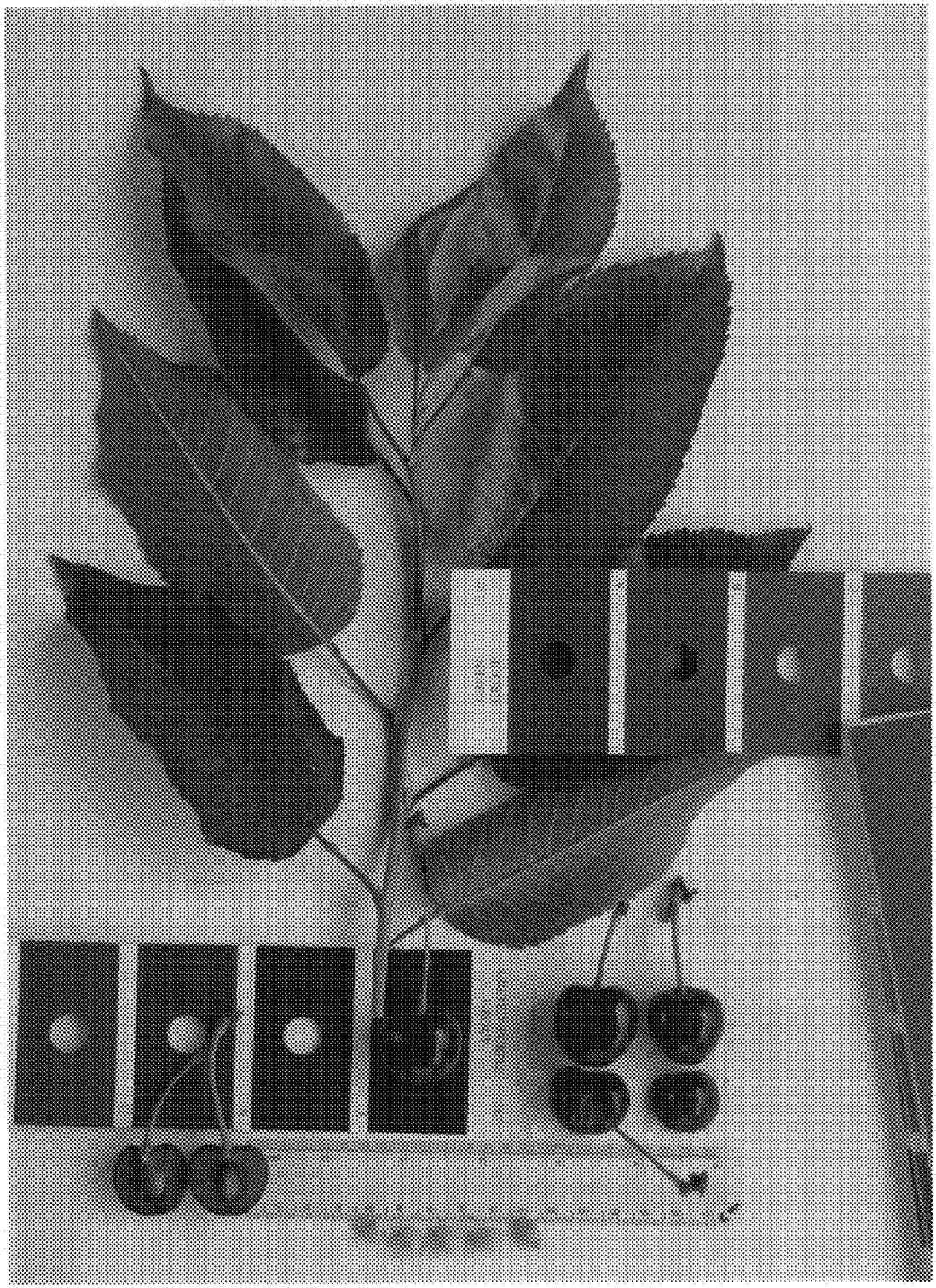

* * * * *